United States Patent
Boga et al.

(10) Patent No.: US 8,012,761 B2
(45) Date of Patent: Sep. 6, 2011

(54) DETECTION OF FORMALDEHYDE IN URINE SAMPLES

(75) Inventors: Rameshbabu Boga, Alpharetta, GA (US); Stephanie M. Martin, Woodstock, GA (US); Molly K. Smith, Atlanta, GA (US); Kevin Peter McGrath, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 623 days.

(21) Appl. No.: 11/638,760

(22) Filed: Dec. 14, 2006

(65) Prior Publication Data

US 2008/0145947 A1 Jun. 19, 2008

(51) Int. Cl.
*G01N 33/52* (2006.01)
*G01N 21/01* (2006.01)
*G01N 21/78* (2006.01)

(52) U.S. Cl. .......... 436/169; 436/130; 436/128; 435/28; 435/25; 435/20; 435/4

(58) Field of Classification Search .................. 436/169, 436/128, 130; 435/28, 25, 20, 4; 135/28, 135/25, 20, 4
See application file for complete search history.

(56) References Cited

U.S. PATENT DOCUMENTS

| | | | |
|---|---|---|---|
| 3,409,405 A * | 11/1968 | Mohan et al. ................. | 436/130 |
| 3,446,599 A | 5/1969 | Shand | |
| 3,630,680 A | 12/1971 | Rittersdorf et al. | |
| 3,712,853 A | 1/1973 | Rittersdorf et al. | |
| 3,802,842 A | 4/1974 | Lange et al. | |
| 3,814,586 A | 6/1974 | Fraser, Jr. et al. | |
| 3,850,576 A | 11/1974 | Rittersdorf et al. | |
| 3,853,466 A | 12/1974 | Rittersdorf et al. | |
| 3,853,471 A | 12/1974 | Rittersdorf et al. | |
| 3,853,472 A | 12/1974 | Rittersdorf et al. | |
| 3,853,476 A | 12/1974 | Rittersdorf et al. | |

(Continued)

FOREIGN PATENT DOCUMENTS

CN 1487296 4/2004

(Continued)

OTHER PUBLICATIONS

Machine Translation of JP 2005-003673 to Sano. Jan. 6, 2005.*
Bosque-Sendra et al., Optimizig analytical methods using sequential response surface methodology. Application to the pararosaniline determination of formandehyde, Fresenius J anal Chem, 2001, 369, 715-718.*
Search Report and Written Opinion for PCT/IB2007/053957 dated Mar. 19, 2008.

(Continued)

*Primary Examiner* — Christine T Mui
(74) *Attorney, Agent, or Firm* — Dority & Manning, P.A.

(57) ABSTRACT

A method for rapidly detecting the presence of formaldehyde in a urine sample (e.g., urine or a urinary material associated therewith, such as headspace gas located associated with urine) is provided. The method includes contacting the urine sample with a substrate on which is disposed a colorant that is capable of undergoing a detectable color change in the presence of formaldehyde. Without intending to be limited by theory, it is believed that oxidation of the colorant by formaldehyde induces either a shift of the absorption maxima towards the red end of the spectrum ("bathochromic shift") or towards the blue end of the spectrum ("hypsochromic shift"). The absorption shift provides a color difference that is detectable, either visually or through instrumentation, to indicate the presence of formaldehyde within the urine sample. For example, prior to contact with a urine sample, the colorant may be colorless or it may possess a certain color. However, after contacting the urine sample and reacting with formaldehyde, the colorant exhibits a color that is different than its initial color. The color change may thus be readily correlated to the presence of formaldehyde in the urine sample.

22 Claims, 7 Drawing Sheets

U.S. PATENT DOCUMENTS

| | | | |
|---|---|---|---|
| 3,880,588 A | 4/1975 | Rittersdorf et al. | |
| 3,945,798 A * | 3/1976 | Young | 436/130 |
| 3,989,462 A | 11/1976 | Hirsch | |
| 4,013,416 A | 3/1977 | Rittersdorf et al. | |
| 4,158,546 A | 6/1979 | Lam et al. | |
| 4,161,507 A | 7/1979 | Hirsch | |
| 4,190,419 A | 2/1980 | Bauer | |
| 4,290,771 A | 9/1981 | Hirsch | |
| 4,345,911 A | 8/1982 | Kohl | |
| 4,385,114 A | 5/1983 | Güthlein et al. | |
| 4,393,881 A * | 7/1983 | Shah | 600/573 |
| 4,665,038 A | 5/1987 | Sakata et al. | |
| 4,703,017 A | 10/1987 | Campbell et al. | |
| 4,704,116 A | 11/1987 | Enloe | |
| 4,742,011 A | 5/1988 | Blake et al. | |
| 4,743,560 A | 5/1988 | Campbell et al. | |
| 4,753,891 A * | 6/1988 | Thompson et al. | 436/130 |
| 4,835,099 A | 5/1989 | Mize et al. | |
| 4,855,240 A | 8/1989 | Rosenstein et al. | |
| 4,889,816 A | 12/1989 | Davis et al. | |
| 4,904,583 A | 2/1990 | Mapes et al. | |
| 4,916,056 A | 4/1990 | Brown, III et al. | |
| 4,920,045 A | 4/1990 | Okuda et al. | |
| 4,954,435 A | 9/1990 | Krauth | |
| 4,956,302 A | 9/1990 | Gordon et al. | |
| 4,978,625 A | 12/1990 | Wagner et al. | |
| 4,980,298 A | 12/1990 | Blake et al. | |
| 5,073,340 A | 12/1991 | Covington et al. | |
| 5,075,077 A | 12/1991 | Durley, III et al. | |
| 5,075,078 A | 12/1991 | Osikowicz et al. | |
| 5,120,643 A | 6/1992 | Ching et al. | |
| 5,149,622 A | 9/1992 | Brown et al. | |
| 5,185,127 A | 2/1993 | Vonk | |
| 5,192,606 A | 3/1993 | Proxmire et al. | |
| 5,208,143 A | 5/1993 | Henderson et al. | |
| 5,244,631 A | 9/1993 | Morikawa | |
| 5,252,459 A | 10/1993 | Tarcha et al. | |
| 5,275,785 A | 1/1994 | May et al. | |
| 5,399,219 A | 3/1995 | Roessler et al. | |
| 5,428,690 A | 6/1995 | Bacus et al. | |
| 5,453,360 A * | 9/1995 | Yu | 435/28 |
| 5,468,236 A | 11/1995 | Everhart et al. | |
| 5,486,166 A | 1/1996 | Bishop et al. | |
| 5,490,846 A | 2/1996 | Ellis et al. | |
| 5,504,013 A | 4/1996 | Senior | |
| 5,540,796 A | 7/1996 | Fries | |
| 5,573,919 A | 11/1996 | Kearns et al. | |
| 5,591,645 A | 1/1997 | Rosenstein | |
| 5,595,618 A | 1/1997 | Fries et al. | |
| 5,599,661 A | 2/1997 | Senba et al. | |
| 5,602,040 A | 2/1997 | May et al. | |
| 5,610,077 A | 3/1997 | Davis et al. | |
| 5,622,871 A | 4/1997 | May et al. | |
| 5,656,503 A | 8/1997 | May et al. | |
| 5,670,381 A | 9/1997 | Jou et al. | |
| 5,702,377 A | 12/1997 | Collier, IV et al. | |
| 5,714,389 A | 2/1998 | Charlton et al. | |
| 5,736,408 A | 4/1998 | Carter et al. | |
| 5,788,863 A | 8/1998 | Milunic | |
| 5,798,273 A | 8/1998 | Shuler et al. | |
| 5,931,823 A | 8/1999 | Stokes et al. | |
| 5,945,281 A | 8/1999 | Prabhu | |
| 5,955,374 A | 9/1999 | Smith et al. | |
| 5,989,924 A | 11/1999 | Root et al. | |
| 5,989,926 A | 11/1999 | Bradley et al. | |
| 5,998,221 A | 12/1999 | Malick et al. | |
| 6,057,165 A | 5/2000 | Mansour | |
| 6,060,638 A | 5/2000 | Paul et al. | |
| 6,077,669 A | 6/2000 | Little et al. | |
| 6,130,100 A | 10/2000 | Jobling et al. | |
| 6,133,048 A | 10/2000 | Penfold et al. | |
| 6,150,002 A | 11/2000 | Varona | |
| 6,156,271 A | 12/2000 | May | |
| 6,165,797 A * | 12/2000 | Halstead | 436/128 |
| 6,187,269 B1 | 2/2001 | Lancesseru et al. | |
| 6,194,220 B1 | 2/2001 | Malick et al. | |
| 6,203,496 B1 | 3/2001 | Gael et al. | |
| 6,234,241 B1 | 5/2001 | Elmore | |
| 6,274,324 B1 | 8/2001 | Davis et al. | |
| 6,294,391 B1 | 9/2001 | Bradley et al. | |
| 6,399,398 B1 | 6/2002 | Cunningham et al. | |
| 6,436,659 B1 * | 8/2002 | Hui et al. | 435/31 |
| 6,436,716 B1 * | 8/2002 | Wu | 436/128 |
| 6,464,635 B1 | 10/2002 | Jimenez Cerrato et al. | |
| 6,524,864 B2 | 2/2003 | Fernandez de Castro | |
| 6,627,459 B1 | 9/2003 | Tung et al. | |
| 6,653,149 B1 | 11/2003 | Tung et al. | |
| 6,663,611 B2 | 12/2003 | Blaney et al. | |
| 6,669,908 B2 | 12/2003 | Weyker et al. | |
| RE38,430 E | 2/2004 | Rosenstein | |
| 6,689,617 B1 | 2/2004 | Abels | |
| 6,713,660 B1 | 3/2004 | Roe et al. | |
| 6,777,243 B2 | 8/2004 | Fukuoka et al. | |
| 6,951,631 B1 | 10/2005 | Catt et al. | |
| 7,044,919 B1 | 5/2006 | Catt et al. | |
| 7,052,831 B2 | 5/2006 | Fletcher et al. | |
| 2002/0042149 A1 | 4/2002 | Butilin et al. | |
| 2002/0045273 A1 | 4/2002 | Butlin et al. | |
| 2003/0119202 A1 | 6/2003 | Kaylor et al. | |
| 2003/0119204 A1 | 6/2003 | Wei et al. | |
| 2003/0124739 A1 | 7/2003 | Song et al. | |
| 2004/0102750 A1 | 5/2004 | Jameson | |
| 2004/0121334 A1 | 6/2004 | Wei et al. | |
| 2004/0121480 A1 | 6/2004 | Wei et al. | |
| 2004/0151632 A1 | 8/2004 | Bradley et al. | |
| 2004/0161859 A1 | 8/2004 | Guo et al. | |
| 2005/0029924 A1 | 2/2005 | Okay et al. | |
| 2005/0036148 A1 | 2/2005 | Phelan et al. | |
| 2005/0037510 A1 | 2/2005 | Sharrock et al. | |
| 2005/0054255 A1 | 3/2005 | Morman et al. | |
| 2005/0059941 A1 | 3/2005 | Baldwin et al. | |
| 2005/0109951 A1 | 5/2005 | Fish et al. | |
| 2005/0112635 A1 | 5/2005 | Gentle et al. | |
| 2005/0112779 A1 | 5/2005 | Wei et al. | |
| 2005/0112780 A1 | 5/2005 | Song | |
| 2005/0124072 A1 * | 6/2005 | Boga et al. | 436/111 |
| 2005/0191704 A1 | 9/2005 | Boga et al. | |
| 2006/0025732 A1 | 2/2006 | Ying et al. | |
| 2006/0127886 A1 | 6/2006 | Kaylor et al. | |
| 2006/0127924 A1 | 6/2006 | Hellyer et al. | |
| 2006/0223193 A1 | 10/2006 | Song et al. | |
| 2006/0240569 A1 | 10/2006 | Goldenbaum et al. | |
| 2006/0246601 A1 | 11/2006 | Song et al. | |
| 2007/0048807 A1 | 3/2007 | Song | |

FOREIGN PATENT DOCUMENTS

| | | | |
|---|---|---|---|
| DE | 3732504 A1 | 4/1989 | |
| EP | 0555045 A1 | 8/1993 | |
| EP | 1034758 A1 | 9/2000 | |
| JP | 2003254959 A | 9/2003 | |
| JP | 2005003673 A | 1/2005 | |
| JP | 2006275817 A | 10/2006 | |
| WO | WO 9000737 A1 | 1/1990 | |
| WO | WO 9516425 A1 | 6/1995 | |
| WO | WO 03019178 A2 | 3/2003 | |
| WO | WO 03019178 A3 | 3/2003 | |
| WO | WO 2004111635 A1 | 12/2004 | |
| WO | WO 2005/016425 A1 | 2/2005 | |

OTHER PUBLICATIONS

Article—Macroscopic Urinalysis (Chemstrip 10) Universtiy of Michigan, http://www.pathology.med.umich.edu/poc/onsite/poc-chemstrip-10.html.

Research Article—Analysis of formaldehyde in the headspace of urine from bladder and prostate cancer patients using selected ion flow tube mass spectrometry, Rapid Commun. Mass Spectrom., 1999; 13;1354-9.

Research article: Selective measurement of HCHO in urine using direct liquid-phase fluorimetric analysis, Clin. Chem. Lab. Med. 2005; 42(2); 178-182.

* cited by examiner

DETECTION OF FORMALDEHYDE IN URINE SAMPLES

BACKGROUND OF THE INVENTION

Studies indicate that the presence of certain levels of formaldehyde in urine can serve as an indicator of cancer in the urogenital system such as, for example, bladder cancer and prostate cancer. See, e.g., Spanel P, et al., Analysis of formaldehyde in the headspace of urine from bladder and prostate cancer patients using selected ion flow tube mass spectrometry, Rapid Commun. Mass Spectrom., 1999; 13; 1354-9. The increase in formaldehyde levels is likely the result of certain cancer cell types that produce an elevated concentration of formaldehyde in the region surrounding the cell. Testing for the presence of formaldehyde can be accomplished by testing a liquid urine sample directly or by testing the vapor over a liquid urine sample, sometimes referred to as headspace testing.

Various methods have been formulated for detecting formaldehyde in urine. For example, U.S. Pat. No. 6,689,617 describes a multistep procedure that includes at least a ten minute mixing step and a period for reagent preparation of at least 24 hours. Techniques involving canines (Willis C. et al., Olfactory detection of human bladder cancer by dogs: proof principle study, BMJ 2004; 329), mass spectrometry (Spanel P, et al., Analysis of formaldehyde in the headspace of urine from bladder and prostate cancer patients using selected ion flow tube mass spectrometry, Rapid Commun Mass Spectrom, 1999; 13; 1354-9), and flourimetric analysis (Short L., Selective measurement of HCHO in urine using direct liquid-phase fluorimetric analysis, Clin. Chem. Lab. Med. 2005; 42(2); 178-182) have also been described. Unfortunately, these methods include time consuming steps requiring specially trained personnel to perform and otherwise require resources or equipment not readily available to many care providers. In addition, it appears that each of these methods require collection of a urine sample from a patient. Such may not be practical in circumstances involving children, incapacitated patients, or the elderly.

As such, a need currently exists for a simple technique for detecting the presence of formaldehyde in urine. A technique that can be easily and quickly conducted in real time without the necessity of expensive equipment would also be beneficial. A technique that can be integrated into personal care products designed to receive and contain urine would also be particularly beneficial.

SUMMARY OF THE INVENTION

In accordance with one embodiment of the present invention, a method for detecting formaldehyde in a urine sample (e.g., urine or a urinary material associated therewith, such as headspace gas located associated with urine) is provided. The method comprises contacting the sample with a substrate, the substrate comprising at least one colorant configured for producing a spectral response when subjected to formaldehyde, detecting the spectral response, and correlating the spectral response to the presence of formaldehyde in the sample.

In another embodiment of the present invention, a device is provided for detecting the presence of formaldehyde in a urine sample. The device comprises a container having an interior volume for the receipt of the liquid sample, a lid configured for enclosing the interior volume of the container, and a substrate affixed to the lid, the substrate comprising a colorant configured for producing a spectral response when subjected to formaldehyde in a vapor over the urine sample.

In still another embodiment of the present invention, an absorbent article is provided for receiving a bodily fluid suspected of containing formaldehyde. The article comprises a substantially liquid impermeable layer, a liquid permeable layer, an absorbent core positioned between the substantially liquid impermeable layer and the liquid permeable layer, and a substrate integrated into the article and positioned such that the substrate is in fluid communication with the bodily fluid when provided by a wearer of the article. The substrate comprises a colorant configured for exhibiting a spectral response indicative of the presence of formaldehyde in the bodily fluid.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figure in which.

Repeat use of reference characters in the present specification and drawing is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Definitions

As used herein, the term "formaldehyde" is intend to encompass formaldehyde in any form, includes its gaseous form (i.e., $H_2CO$), hydrated form (i.e., $CH_2(OH)_2$), and so forth.

As used herein, the term "urine sample" generally refers to urine or a urinary material associated therewith (e.g., headspace gas located associated with urine). The urine and/or urinary material may be used as obtained or pretreated in some manner. For example, such pretreatment may include filtration, precipitation, dilution, distillation, mixing, concentration, inactivation of interfering components, the addition of reagents, lysing, etc.

Detailed Description

Generally speaking, the present invention is directed to a method for rapidly etecting the presence of formaldehyde in a urine sample. The method includes contacting the urine sample with a substrate on which is disposed a colorant that is capable of undergoing a detectable color change in the presence of formaldehyde. Without intending to be limited by theory, it is believed that oxidation of the colorant by formaldehyde induces either a shift of the absorption maxima towards the red end of the spectrum ("bathochromic shift") or towards the blue end of the spectrum ("hypsochromic shift"). The absorption shift provides a color difference that is detectable, either visually or through instrumentation, to indicate the presence of formaldehyde within the urine sample. For example, prior to contact with a urine sample, the colorant may be colorless or it may possess a certain color. However, after contacting the urine sample and reacting with formaldehyde, the colorant exhibits a color that is different than its initial color. The color change may thus be readily correlated to the presence of formaldehyde in the urine sample.

A variety of colorants (e.g., dyes, pigments, etc.) may be employed in the present invention. For example, arylmethanes (e.g., diarylmethanes and triarylmethanes) are particularly suitable colorants for use in the present invention. Triarylmethanes, for example, have the following general structure:

wherein R, R', and R" are independently selected from substituted and unsubstituted aryl groups, such as phenyl, naphthyl, anthracenyl, etc. The aryl groups may be substituted with functional groups, such as amino, hydroxyl, carbonyl, carboxyl, sulfonic, alkyl, and/or other known functional groups. Examples of such triarylmethane leuco bases include basic fuchsin, pararosanilin (Magenta 0), rosanilin (magenta I), magenta II, new fuchsin ("magenta III"), methyl violet 2B, methyl violet 6B, methyl violet 10B ("crystal violet"), methyl green, ethyl green, acid fuchsin, and so forth etc. Suitable diarylmethane leuco bases may include 4,4'-bis (dimethylamino) benzhydrol (also known as "Michler's hydrol"), Michler's hydrol leucobenzotriazole, Michler's hydrol leucomorpholine, Michler's hydrol leucobenzenesulfonamide, etc. In one particular embodiment, the colorant may include pararosanilin or an analog thereof. The structure of pararosanilin is set forth below:

Although pararosanilin may itself react with formaldehyde to provide a detectable color change, it is often desired that it is pre-reacted with a sulfur-containing compound to enhance the degree to which the color change occurs. For example, the unreacted colorant may be colorless and the reacted colorant may exhibit a certain color (e.g., red). Suitable sulfur-containing compounds for use in the present invention may include, for instance, sulfuric acid, sulfosalicylic acid, sulfonic acids, such as methanesulfonic acid, benzenesulfonic acid, toluenesulfonic acid, trifluoromethanesulfonic acid, styrenesulfonic acid, naphthalene disulfonic acid, hydroxybenzenesulfonic acid, etc.; and so forth. In one particular embodiment, for example, pararosanilin may be treated with sulfuric acid, which results in the addition of a sulfonic acid group on the central carbon atom. The structure of such a "sulfo-pararosanilin" is set forth below:

Sulfo-pararosanilin is generally colorless. However, upon reaction with formaldehyde, the colorant may undergo a change in color to a pink or reddish color. This allows a user to readily detect the presence of formaldehyde. Nevertheless, other colorants may be employed in some embodiments of the present invention to form a more intense color. Such colorants may include, for instance, analogs of pararosanilin (e.g., rosanilin (magenta I), magenta II, new fuchsin ("magenta III"), etc.). In one particular embodiment, for example, basic fuchsin is employed in the present invention, which is believed to be a mixture of pararosanilin, rosanilin (magenta I), and magenta II.

Yet another suitable class of colorants that may be employed with the substrate of the present invention is aromatic azo compounds having the general structure:

X—R$_1$—N=N—R$_2$—Y wherein,

R$_1$ is an aromatic group;

R$_2$ is selected from the group consisting of aliphatic and aromatic groups; and X and Y are independently selected from the group consisting of hydrogen, halides, —NO$_2$, —NH$_2$, aryl groups, alkyl groups, alkoxy groups, sulfonate groups, —SO$_3$H, —OH, —COH, —COOH, halides, etc. Also suitable are azo derivatives, such as azoxy compounds (X—R$_1$—N=NO—R$_2$—Y) or hydrazo compounds (X—R$_1$—NH—N H—R$_2$—Y). Particular examples of such azo compounds (or derivatives thereof) include Methyl Violet, Methyl Yellow, Methyl Orange, Methyl Red, and Methyl Green. By way of example, chrysoidin (4-phenylazo-1,3-phenylenediamine monohydrochloride) is a colorant from this class that may be used with the present invention.

To achieve the desired color change in accordance with the present invention, the colorant may be applied to a substrate so that a user to readily detect the change in color that occurs upon reacting with formaldehyde. For example, a solution containing the colorant may be initially applied to the substrate within a detection zone. The colorant solution may contain an aqueous and/or non-aqueous solvent depending on the material used to form the chromatographic medium. Suitable non-aqueous solvents may include glycols (e.g., propylene glycol, butylene glycol, triethylene glycol, hexylene glycol, polyethylene glycols, ethoxydiglycol, and dipropyleneglycol); alcohols (e.g., methanol, ethanol, n-propanol, and isopropanol); triglycerides; ethyl acetate; acetone;

triacetin; acetonitrile, tetrahydrafuran; xylenes; formaldehydes (e.g., dimethylformamide); etc. The amount of the solvent and colorant in the solution may generally vary based on the desired level of sensitivity. For instance, in some embodiments, the colorant may be present in the solution at a concentration of from about 0.001 wt. % to about 1 wt. %, in some embodiments from about 0.005 wt. % to about 0.5 wt. %, and in some embodiments, from about 0.01 wt. % to about 0.5 wt. %.

Besides the colorant and solvent, other components may also be employed in the solution. For example, surfactants may help enhance the sensitivity of the colorant and the contrast between different regions. Particularly desired surfactants are nonionic surfactants, such as ethoxylated alkylphenols, ethoxylated and propoxylated fatty alcohols, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, acetylenic diols, and mixtures thereof. Various specific examples of suitable nonionic surfactants include, but are not limited to, methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$-$C_{22}$) alcohol, including 3 to 20 ethylene oxide moieties, polyoxyethylene-20 isohexadecyl ether, polyoxyethylene-23 glycerol laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxyethylene-6 tridecyl ether, laureth-2, laureth-3, laureth-4, PEG-3 castor oil, PEG 600 dioleate, PEG 400 dioleate, and mixtures thereof. Commercially available nonionic surfactants may include the SURFYNOL® range of acetylenic diol surfactants available from Air Products and Chemicals of Allentown, Pa. and the TWEEN® range of polyoxyethylene surfactants available from Fischer Scientific of Pittsburgh, Pa.

A binder may also be employed to facilitate the immobilization of the colorant on a substrate. For example, water-soluble organic polymers may be employed as binders. One suitable class of water-soluble organic polymers includes polysaccharides and derivatives thereof. Polysaccharides are polymers containing repeated carbohydrate units, which may be cationic, anionic, nonionic, and/or amphoteric. In one particular embodiment, the polysaccharide is a nonionic, cationic, anionic, and/or amphoteric cellulosic ether. Suitable nonionic cellulosic ethers may include, but are not limited to, alkyl cellulose ethers, such as methyl cellulose and ethyl cellulose; hydroxyalkyl cellulose ethers, such as hydroxyethyl cellulose, hydroxypropyl cellulose, hydroxypropyl hydroxybutyl cellulose, hydroxyethyl hydroxypropyl cellulose, hydroxyethyl hydroxybutyl cellulose and hydroxyethyl hydroxypropyl hydroxybutyl cellulose; alkyl hydroxyalkyl cellulose ethers, such as methyl hydroxyethyl cellulose, methyl hydroxypropyl cellulose, ethyl hydroxyethyl cellulose, ethyl hydroxypropyl cellulose, methyl ethyl hydroxyethyl cellulose and methyl ethyl hydroxypropyl cellulose; and so forth.

The substrate of the present invention is desirably formed from a solid, but not necessarily rigid, material. The solid support may be formed from any of a variety materials, such as a film, paper, nonwoven web, knitted fabric, woven fabric, foam, glass, etc. For example, the materials used to form the solid support may include, but are not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth.

The colorant solution may be applied to the substrate using any known application technique, such as printing, dipping, spraying, melt extruding, coating (e.g., solvent coating, powder coating, brush coating, etc.), and so forth. Upon application, the solution is dried to remove the carrier and leave a residue of the colorant for interacting with formaldehyde.

Regardless of the manner in which it is applied, the amount of the colorant employed is effective to result in a detectable color change upon contact with formaldehyde. The exact quantity of a colorant employed within a particular location may vary based on a variety of factors, including the sensitivity of the colorant, the presence of other additives, the desired degree of detectability (e.g., with an unaided eye), and the suspected concentration of formaldehyde in the urine sample. For instance, a certain minute amount of formaldehyde may be normally present in a urine sample or may be expected due to a diet of foods rich in free or chemically bound formaldehyde. Thus, colorants may be employed in an amount sufficient to provide a spectral response, such as a detectable color change, in the presence of formaldehyde at certain threshold concentrations, such as about 10 parts per billion or more of the urine sample. Of course, the threshold concentration may vary depending on the nature of the urine sample. For instance, the threshold concentration in the headspace gas above urine may be about 10 parts per billion, while the threshold concentration may be about $1\times10^6$ or more in urine. Regardless, when present on a substrate, the colorant typically constitutes from about 0.001 wt. % to about 20 wt. %, in some embodiments from about 0.01 wt. % to about 10 wt. %, and in some embodiments from about 0.1 wt. % to about 5 wt. % of the dry weight of the substrate. The amount of other additives (e.g., surfactants, binders, etc.) may also vary as desired, such as from about 0.001 wt. % to about 10 wt. %, in some embodiments from about 0.01 wt. % to about 5 wt. %, and in some embodiments from about 0.025 wt. % to about 1 wt. % based on the dry weight of the substrate.

If desired, a detection zone may be formed on the substrate so that a user may better determine the presence of formaldehyde within a urine sample. Desirably, the detection zone possesses a size effective to permit visual observation without unduly increasing the size of the substrate. The width (or diameter) of the detection zone may, for example, range from about 0.01 to about 100 millimeters, in some embodiments from about 0.1 to about 50 millimeters, and in some embodiments, from about 1 to about 20 millimeters. The shape of the detection zone may also enhance visual observation of the colorant as an indicator. For example, the detection zone may be in the form of stripes, bands, dots, or any other geometric shape.

Multiple colorants may also be used to provide a semi-quantitative test to indicate not only the presence of formaldehyde but also the amount within a urine sample. More specifically, multiple detection zones representing various levels of sensitivity for particular concentrations of formaldehyde may be formed on the substrate. By way of example, three detection zones might be formed on the substrate at three different locations with such zones representing sensitivities for a low, medium, and high concentration of formaldehyde. Upon testing a particular sample having a medium concentration of formaldehyde, only the low and medium colorant would provide a spectral response. Knowing the predetermined sensitivity of each colorant would then allow a correlation to determine at least a range for the concentration of formaldehyde present in the urine sample.

One or more control colorants may also be used with the present invention. For example, a colorant may be located on the substrate at a location where it will not make contact with the urine sample. When the substrate is to be dipped into a liquid urine sample, colorant may be located at two separate locations along the substrate so that only one may be dipped into the liquid to be tested. By way of further example, the colorant used for the control may also be placed on a separate substrate (for example, as part of a kit) that will not make contact with the urine sample but will be readily accessible during testing for purposes of comparison with a colorant that is subjected to the urine sample. Such a configuration may be particularly appropriate where a urine sample's headspace is being tested in order to avoid contact of the control with the vapor.

To test a sample for the presence of formaldehyde, the substrate of the present invention, bearing one or more colorants as discussed above, is contacted with the urine sample of interest. Such contact may be by immersing all or part of the substrate into a urine sample such as a liquid specimen containing the urine to be tested. Alternatively, the substrate might be positioned within an absorbent article that is worn by a test subject, where the substrate is positioned so as to come into contact with urine discharged by the subject. The location where the colorant is present on the sample may be placed into direct contact with the liquid sample or, alternatively, the substrate may be constructed so that liquid migrates or flows from a part of the substrate contacted with the liquid to a location on the substrate bearing the colorant. In yet another alternative, the substrate may be positioned in the headspace or vapor above a liquid sample containing the urine to be tested.

The degree to which the colorant changes color provides information (a spectral response) regarding the presence of formaldehyde to which it is exposed. For example, basic fuchsin may undergo a significant color change from colorless to pink in the presence of formaldehyde. In the presence of other aldehydes (e.g., acetaldehyde, isovaleraldehyde, phenylacetalaldehyde, or phthalic dicarboxyaldehyde), the color change occurs to a lesser extent if at all. Thus, when a urine sample is placed in to contact with the colorant, a color change may simply be observed to determine whether the infection is caused by formaldehyde. That is, if the color change occurs to a certain degree (e.g., from colorless to pink), it may be determined that the infected urine sample contains formaldehyde.

The color change may be observed visually, with the help of an instrument, or both. In one exemplary embodiment of the present invention, the spectral response is measured with an optical reader. The actual configuration and structure of the optical reader may generally vary as is readily understood by those skilled in the art. Typically, the optical reader contains an illumination source that is capable of emitting electromagnetic radiation and a detector that is capable of registering a signal (e.g., transmitted or reflected light). The illumination source may be any device known in the art that is capable of providing electromagnetic radiation, such as light in the visible or near-visible range (e.g., infrared or ultraviolet light). For example, suitable illumination sources that may be used in the present invention include, but are not limited to, light emitting diodes (LED), flashlamps, cold-cathode fluorescent lamps, electroluminescent lamps, and so forth. The illumination may be multiplexed and/or collimated. In some cases, the illumination may be pulsed to reduce any background interference. Further, illumination may be continuous or may combine continuous wave (CW) and pulsed illumination where multiple illumination beams are multiplexed (e.g., a pulsed beam is multiplexed with a CW beam), permitting signal discrimination between a signal induced by the CW source and a signal induced by the pulsed source. For example, in some embodiments, LEDs (e.g., aluminum gallium arsenide red diodes, gallium phosphide green diodes, gallium arsenide phosphide green diodes, or indium gallium nitride violet/blue/ultraviolet (UV) diodes) are used as the pulsed illumination source. One commercially available example of a suitable UV LED excitation diode suitable for use in the present invention is Model NSHU550E (Nichia Corporation), which emits 750 to 1000 microwatts of optical power at a forward current of 10 milliamps (3.5-3.9 volts) into a beam with a full-width at half maximum of 10 degrees, a peak wavelength of 370-375 nanometers, and a spectral half-width of 12 nanometers.

In some cases, the illumination source may provide diffuse illumination to the colorant. For example, an array of multiple point light sources (e.g., LEDs) may simply be employed to provide relatively diffuse illumination. Another particularly desired illumination source that is capable of providing diffuse illumination in a relatively inexpensive manner is an electroluminescent (EL) device. An EL device is generally a capacitor structure that utilizes a luminescent material (e.g., phosphor particles) sandwiched between electrodes, at least one of which is transparent to allow light to escape. Application of a voltage across the electrodes generates a changing electric field within the luminescent material that causes it to emit light.

The detector may generally be any device known in the art that is capable of sensing a spectral response. For instance, the detector may be an electronic imaging detector that is configured for spatial discrimination. Some examples of such electronic imaging sensors include high speed, linear charge-coupled devices (CCD), charge-injection devices (CID), complementary-metal-oxide-semiconductor (CMOS) devices, and so forth. Such image detectors, for instance, are generally two-dimensional arrays of electronic light sensors, although linear imaging detectors (e.g., linear CCD detectors) that include a single line of detector pixels or light sensors, such as, for example, those used for scanning images, may also be used. Each array includes a set of known, unique positions that may be referred to as "addresses." Each address in an image detector is occupied by a sensor that covers an area (e.g., an area typically shaped as a box or a rectangle). This area is generally referred to as a "pixel" or pixel area. A detector pixel, for instance, may be a CCD, CID, or a CMOS sensor, or any other device or sensor that detects or measures light. The size of detector pixels may vary widely, and may in some cases have a diameter or length as low as 0.2 micrometers.

In other embodiments, the detector may be a light sensor that lacks spatial discrimination capabilities. For instance, examples of such light sensors may include photomultiplier devices, photodiodes, such as avalanche photodiodes or silicon photodiodes, and so forth. Silicon photodiodes are sometimes advantageous in that they are inexpensive, sensitive, capable of high-speed operation (short risetime/high bandwidth), and easily integrated into most other semiconductor technology and monolithic circuitry. In addition, silicon photodiodes are physically small, which enables them to be readily incorporated into various types of detection systems. If silicon photodiodes are used, then the wavelength range of the emitted signal may be within their range of sensitivity, which is 400 to 1100 nanometers.

Optical readers may generally employ any known detection technique, including, for instance, luminescence (e.g., fluorescence, phosphorescence, etc.), absorbance (e.g., fluorescent or non-fluorescent), diffraction, etc. In one particular embodiment of the present, the optical reader measures color intensity of a spectral response as a function of absorbance. In one embodiment, absorbance readings are measured using a microplate reader from Dynex Technologies of Chantilly, Va. (Model # MRX). In another embodiment, absorbance readings are measured using a conventional test known as "CIELAB", which is discussed in *Pocket Guide to Digital Printing* by F. Cost, Delmar Publishers, Albany, N.Y. ISBN 0-8273-7592-1 at pages 144 and 145. This method defines three variables, L*, a*, and b*, which correspond to three characteristics of a perceived color based on the opponent theory of color perception. The three variables have the following meaning:

L*=Lightness (or luminosity), ranging from 0 to 100, where 0=dark and 100=light;

a*=Red/green axis, ranging approximately from −100 to 100; positive values are reddish and negative values are greenish; and b*=Yellow/blue axis, ranging approximately from −100 to 100; positive values are yellowish and negative values are bluish.

Because CIELAB color space is somewhat visually uniform, a single number may be calculated that represents the difference between two colors as perceived by a human. This difference is termed ΔE and calculated by taking the square root of the sum of the squares of the three differences (ΔL*, Δa*, and Δb*) between the two colors. In CIELAB color space, each ΔE unit is approximately equal to a "just noticeable" difference between two colors. CIELAB is therefore a good measure for an objective device-independent color specification system that may be used as a reference color space for the purpose of color management and expression of changes in color. Using this test, color intensities (L*, a*, and b*) may thus be measured using, for instance, a handheld spectrophotometer from Minolta Co. Ltd. of Osaka, Japan (Model # CM2600d). This instrument utilizes the D/8 geometry conforming to CIE No. 15, ISO 7724/1, ASTME1164 and JIS Z8722-1982 (diffused illumination/8-degree viewing system. The D65 light reflected by the specimen surface at an angle of 8 degrees to the normal of the surface is received by the specimen-measuring optical system. Still another suitable optical reader is the reflectance spectrophotometer described in U.S. Pat. App. Pub. No. 2003/0119202 to Kaylor, et al., which is incorporated herein in its entirety by reference thereto for all purposes. Likewise, transmission-mode detection systems may also be used in the present invention.

In certain embodiments, the spectral response of the colorant of the present invention may be rapid and may be detected within a relatively short period of time. For example, the spectral response may occur in about 20 minutes or less, in some embodiments about 10 minutes or less, in some embodiments about 5 minutes or less, in some embodiments about 3 minutes or less, and in some embodiments, from about 10 seconds to about 2 minutes. In this manner, the colorant may provide a "real-time" indication of the presence of formaldehyde in the sample.

Figure 1A:
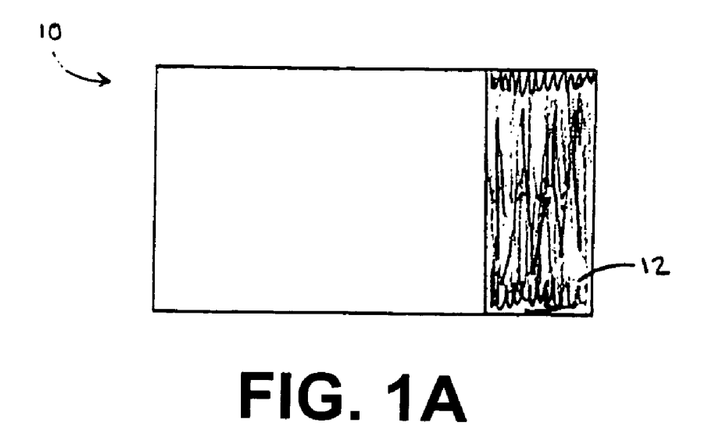
FIG. 1 contains schematic representations of exemplary embodiments of various substrates according to the present invention.
Figure 1B:
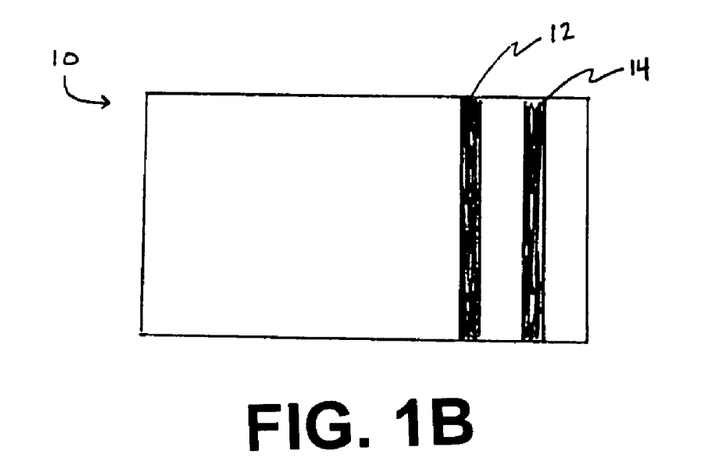
Figure 1C:
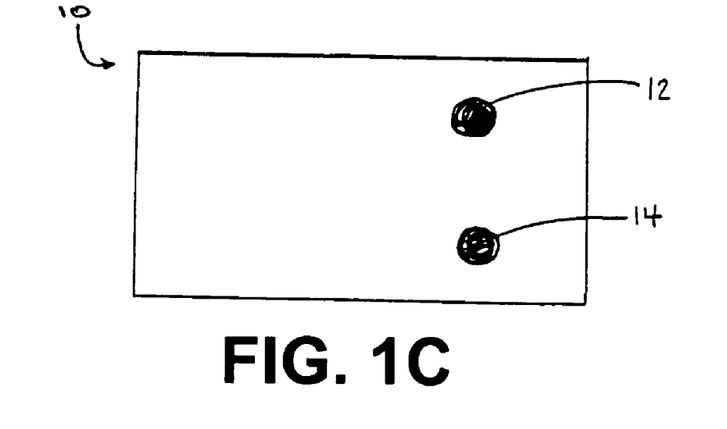

The above-described techniques may be implemented in a variety of ways in accordance with the present invention. Referring now to FIG. 1, for instance, an exemplary embodiment of a substrate 10 according to the present invention is illustrated. In FIG. 1A, substrate 10 has a strip-like shape and is shown having a block of colorant 12 applied along one end. FIG. 1B shows colorant 12 and colorant 14 applied as thin bands along one end of substrate 10. Colorant 12 and colorant 14 are applied to the substrate 10 as a series of dots in FIG. 1C. It should be understood that these figures serve only as illustrative examples. Numerous other configurations for the colorant and the shape of substrate 10 are possible as previously described. Furthermore, although shown as a darkened area in the figures, the colorant may actually be colorless when first applied to substrate 10 so as to undergo a color and/or shade change after being subjected to the presence of formaldehyde.

Figure 2:
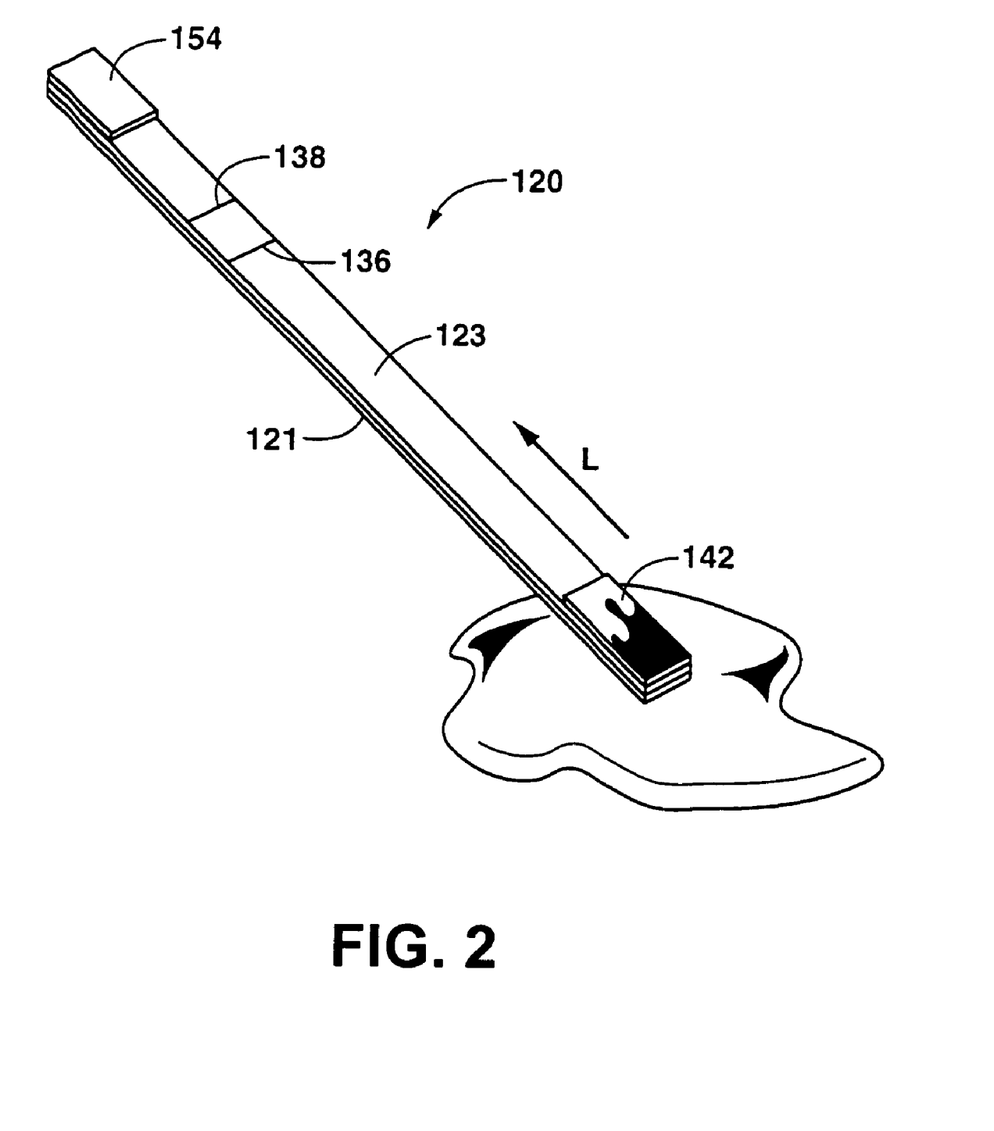
FIG. 2 contains a perspective view of an exemplary embodiment of a substrate comprising a lateral flow device according to the present invention.

FIG. 2 illustrates another exemplary embodiment of the present invention in which the substrate is constructed as a lateral flow device 120 for detecting the presence of formaldehyde in accordance with the present invention. As shown, the lateral flow device 120 contains a chromatographic medium 123 optionally supported by a rigid support material 121. A colorant 136, constructed as previously described, is also applied to medium 123. The chromatographic medium 123 may be made from any of a variety of materials through which the urine sample is capable of passing. For example, the chromatographic medium 123 may be a porous membrane formed from synthetic or naturally occurring materials, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. In one particular embodiment, the chromatographic medium 123 is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The size and shape of the chromatographic medium 123 may generally vary as is readily recognized by those skilled in the art. For instance, a porous membrane strip may have a length of from about 10 to about 100 millimeters, in some embodiments from about 20 to about 80 millimeters, and in some embodiments, from about 40 to about 60 millimeters. The width of the membrane strip may also range from about 0.5 to about 20 millimeters, in some embodiments from about 1 to about 15 millimeters, and in some embodiments, from about 2 to about 10 millimeters. Likewise, the thickness of the membrane strip is generally small enough to allow transmission-based detection. For example, the membrane strip may have a thickness less than about 500 micrometers, in some embodiments less than about 250 micrometers, and in some embodiments, less than about 150 micrometers.

As stated above, the support 121 carries the chromatographic medium 123. For example, the support 121 may be positioned directly adjacent to the chromatographic medium 123 as shown in FIG. 2, or one or more intervening layers may be positioned between the chromatographic medium 123 and the support 121. Regardless, the support 121 may generally be formed from any material able to carry the chromatographic medium 123. The support 121 may be formed from a material that is transmissive to light, such as transparent or optically diffuse (e.g., transluscent) materials. Also, it is generally desired that the support 121 is liquid-impermeable so that fluid flowing through the medium 123 does not leak through the support 121. Examples of suitable materials for the support include, but are not limited to, glass; polymeric materials, such as polystyrene, polypropylene, polyester (e.g., Mylar® film), polybutadiene, polyvinylchloride, polyamide, polycarbonate, epoxides, methacrylates, and polymelamine; and so forth. To provide a sufficient structural backing for the chromatographic medium 123, the support 121 is generally selected to have a certain minimum thickness. Likewise, the thickness of the support 121 is typically not so large as to adversely affect its optical properties. Thus, for example, the support 121 may have a thickness that ranges from about 100 to about 5,000 micrometers, in some embodiments from about 150 to about 2,000 micrometers, and in some embodiments, from about 250 to about 1,000 micrometers. For instance, one suitable membrane strip having a thickness of about 125 micrometers may be obtained from Millipore Corp. of Bedford, Mass. under the name "SHF18OUB25."

As is well known the art, the chromatographic medium 123 may be cast onto the support 121, wherein the resulting laminate may be die-cut to the desired size and shape. Alternatively, the chromatographic medium 123 may simply be laminated to the support 121 with, for example, an adhesive. In some embodiments, a nitrocellulose or nylon porous membrane is adhered to a Mylar® film. An adhesive is used to bind the porous membrane to the Mylar® film, such as a pressure-sensitive adhesive. Laminate structures of this type are believed to be commercially available from Millipore Corp. of Bedford, Mass. Still other examples of suitable laminate device structures are described in U.S. Pat. No. 5,075,077 to Durley, III, et al., which is incorporated herein in its entirety by reference thereto for all purposes.

The device 120 may also contain an absorbent material 154 that is positioned adjacent to the medium 123. The absorbent material 154 assists in promoting capillary action and fluid flow through the medium 123. In addition, the absorbent material 154 receives fluid that has migrated through the entire chromatographic medium 123 and thus draws any unreacted components away from the detection region. Some suitable absorbent materials that may be used in the present invention include, but are not limited to, nitrocellulose, cellulosic materials, porous polyethylene pads, glass fiber filter paper, and so forth. The absorbent material may be wet or dry prior to being incorporated into the device. Pre-wetting may facilitate capillary flow for some fluids, but is not typically required. Also, as is well known in the art, the absorbent material may be treated with a surfactant to assist the wicking process.

To initiate the test, a user may directly apply the urine sample to a portion of the chromatographic medium 123 through which it may then travel in the direction illustrated by arrow "L" in FIG. 2. Alternatively, the urine sample may first be applied to a sample application zone 142 that is in fluid communication with the chromatographic medium 123. The sample application zone 142 may be formed on the medium 123. Alternatively, as shown in FIG. 2, the sample application zone 142 may be formed by a separate material, such as a pad. Some suitable materials that may be used to form such sample pads include, but are not limited to, nitrocellulose, cellulose, porous polyethylene pads, and glass fiber filter paper. If desired, the sample application zone 142 may also contain one or more pretreatment reagents, either diffusively or non-diffusively attached thereto.

In certain applications, it may be desirable to add an additional reagent when testing a sample using device 120. For such instances, device may 120 may include a reagent zone (not shown) that is in fluid communication with the sample application zone 142. The reagent zone may be formed from a separate material or pad. Such a reagent pad may be formed from any material through which the urine sample is capable of passing, such as glass fibers. Alternatively, the reagent zone may simply be formed on the medium 123. Regardless, the reagent zone may be applied with one or more solutions containing reagents as desired. Thus, the urine sample may contact the reagent zone to mix with the desired reagents before traveling in the direction of arrow L.

One benefit of the lateral flow device of the present invention is its ability to readily incorporate one or more additional zones to facilitate analyte detection. For example, referring again to FIG. 2, an additional colorant 138 may also be employed in the lateral flow device 120 for improving detection accuracy, for providing dual indication of the presence of formaldehyde, and/or for providing a semiquantitative indication of the amount of formaldehyde present in a sample as previously discussed. Additionally, colorant 138 could be configured to provide a spectral response to confirm that testing has been completed regardless of the presence of formaldehyde. For example, colorant 138 could be configured to provide a color change to notify the user that a liquid sample has successfully migrated along the length of device 120 in the direction of arrow L. Among the benefits provided by such a colorant 138 is that the user is informed that a sufficient volume of urine sample has been added without requiring careful measurement or calculation. This provides the ability to use the lateral flow device 120 without the need for externally controlling the reaction time, urine sample volume, etc.

Device 120 is not limited to colorants disposed and oriented in the manner shown in FIG. 2. As previously described, colorants may be generally provided in any number of distinct detection regions as desired. Furthermore, each colorant location may contain the same or different materials. For example, the colorants may include two or more distinct components, formed as lines, dots, etc. In addition, the colorants may be disposed in the form of lines in a direction that is substantially perpendicular to the flow of the urine sample through the device 120 as shown or, in some embodiments, the colorants may be disposed in the form of lines in a direction that is substantially parallel to the flow of the urine sample through the device 120.

In accordance with the present invention, one or more substrates may be integrated into an absorbent article. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, and so forth; medical absorbent articles, such as garments, fenestration materials, underpads, bedpads, bandages, absorbent drapes, and medical wipes; food service wipers; clothing articles; and so forth. Materials and processes suitable for forming such absorbent articles are well known to those skilled in the art. Typically, absorbent articles include a substantially liquid-impermeable layer (e.g., outer cover), a liquid-permeable layer (e.g., bodyside liner, surge layer, etc.), and an absorbent core.

Figure 3:
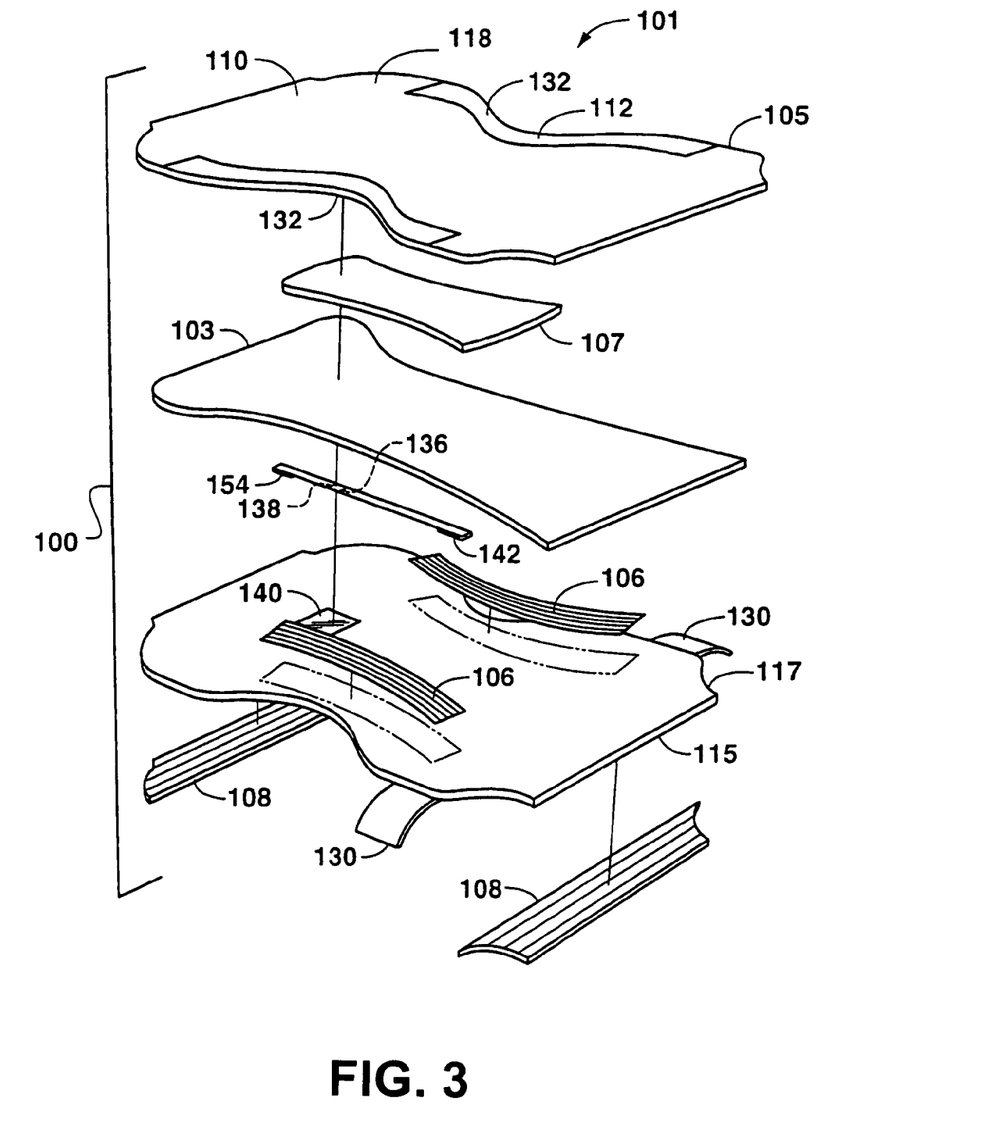
FIGS. 3-7 contain perspective views of exemplary embodiments of absorbent articles incorporating a substrate that comprises a representative lateral flow device according to the present invention.

Various embodiments of an absorbent article that may be formed according to the present invention will now be described in more detail. For purposes of illustration only, an absorbent article is shown in FIG. 3 as an adult incontinence article 101. In the illustrated embodiment, the adult incontinence article 101 is shown as having an hourglass shape in an unfastened configuration. However, other shapes may of course be utilized, such as a generally rectangular shape, T-shape, or I-shape. As shown, the adult incontinence article 101 includes a chassis formed by various components, including an outer cover 117, bodyside liner 105, absorbent core 103, and surge layer 107. It should be understood, however, that other layers may also be used in exemplary embodiments of the present invention. Likewise, one or more of the layers referred to in FIG. 3 may also be eliminated in certain exemplary embodiments of the present invention.

The bodyside liner 105 is generally employed to help isolate the wearer's skin from liquids held in the absorbent core 103. For example, the liner 105 presents a bodyfacing surface that is typically compliant, soft feeling, and non-irritating to the wearer's skin. Typically, the liner 105 is also less hydrophilic than the absorbent core 103 so that its surface remains relatively dry to the wearer. As indicated above, the liner 105 may be liquid-permeable to permit liquid to readily penetrate through its thickness. Exemplary liner constructions that contain a nonwoven web are described in U.S. Pat. No. 5,192,606 to Proxmire, et al.; U.S. Pat. No. 5,702,377 to Collier, IV, et al.; U.S. Pat. No. 5,931,823 to Stokes, et al.; U.S. Pat. No. 6,060,638 to Paul, et al.; and U.S. Pat. No. 6,150,002 to Varona, as well as U.S. Patent Application Publication Nos. 2004/0102750 to Jameson; 2005/0054255 to Morman, et al.; and 2005/0059941 to Baldwin, et al., all of which are incorporated herein in their entirety by reference thereto for all purposes.

The adult incontinence article 101 may also include a surge layer 107 that helps to decelerate and diffuse surges or gushes of liquid that may be rapidly introduced into the absorbent core 103. Desirably, the surge layer 107 rapidly accepts and temporarily holds the liquid prior to releasing it into the storage or retention portions of the absorbent core 103. In the illustrated embodiment, for example, the surge layer 107 is interposed between an inwardly facing surface 116 of the bodyside liner 105 and the absorbent core 103. Alternatively, the surge layer 107 may be located on an outwardly facing surface 118 of the bodyside liner 105. The surge layer 107 is typically constructed from highly liquid-permeable materials. Examples of suitable surge layers are described in U.S. Pat. No. 5,486,166 to Ellis, et al. and U.S. Pat. No. 5,490,846 to Ellis, et al., which are incorporated herein in their entirety by reference thereto for all purposes.

The outer cover 117 is typically formed from a material that is substantially impermeable to liquids. For example, the outer cover 117 may be formed from a thin plastic film or other flexible liquid-impermeable material. In one embodiment, the outer cover 117 is formed from a polyethylene film having a thickness of from about 0.01 millimeter to about 0.05 millimeter. The film may be impermeable to liquids, but permeable to gases and water vapor (i.e., "breathable"). This permits vapors to escape from the absorbent core 103, but still prevents liquid exudates from passing through the outer cover 117. If a more cloth-like feeling is desired, the outer cover 117 may be formed from a polyolefin film laminated to a nonwoven web. For example, a stretch-thinned polypropylene film may be thermally laminated to a spunbond web of polypropylene fibers.

Besides the above-mentioned components, the adult incontinence article 101 may also contain various other components as is known in the art. For example, the adult incontinence article 101 may also contain a substantially hydrophilic tissue wrapsheet (not illustrated) that helps maintain the integrity of the fibrous structure of the absorbent core 103. The tissue wrapsheet is typically placed about the absorbent core 103 over at least the two major facing surfaces thereof, and composed of an absorbent cellulosic material, such as creped wadding or a high wet-strength tissue. The tissue wrapsheet may be configured to provide a wicking layer that helps to rapidly distribute liquid over the mass of absorbent fibers of the absorbent core 103. The wrapsheet material on one side of the absorbent fibrous mass may be bonded to the wrapsheet located on the opposite side of the fibrous mass to effectively entrap the absorbent core 103. Furthermore, the adult incontinence article 101 may also include a ventilation layer (not shown) that is positioned between the absorbent core 103 and the outer cover 117. When utilized, the ventilation layer may help insulate the outer cover 117 from the absorbent core 103, thereby reducing dampness in the outer cover 117. Examples of such ventilation layers may include a nonwoven web laminated to a breathable film, such as described in U.S. Pat. No. 6,663,611 to Blaney, et al., which is incorporated herein in its entirety by reference thereto for all purposes.

In some embodiments, the adult incontinence article 101 may also include a pair of side panels (or ears) (not shown) that extend from the side edges 132 of the adult incontinence article 101 into one of the waist regions. The side panels may be integrally formed with a selected adult incontinence article component. For example, the side panels may be integrally formed with the outer cover 117 or from the material employed to provide the top surface. In alternative configurations, the side panels may be provided by members connected and assembled to the outer cover 117, the top surface, between the outer cover 117 and top surface, or in various other configurations. If desired, the side panels may be elasticized or otherwise rendered elastomeric by use of the elastic nonwoven composite of the present invention. Examples of absorbent articles that include elasticized side panels and selectively configured fastener tabs are described in PCT Patent Application WO 95/16425 to Roessler; U.S. Pat. No. 5,399,219 to Roessler et al.; U.S. Pat. No. 5,540,796 to Fries; and U.S. Pat. No. 5,595,618 to Fries, each of which is incorporated herein in its entirety by reference thereto for all purposes.

As representatively illustrated in FIG. 3, the adult incontinence article 101 may also include a pair of containment flaps 112 that are configured to provide a barrier and to contain the lateral flow of body exudates. The containment flaps 112 may be located along the laterally opposed side edges 132 of the bodyside liner 105 adjacent the side edges of the absorbent core 103. The containment flaps 112 may extend longitudinally along the entire length of the absorbent core 103, or may only extend partially along the length of the absorbent core 103. When the containment flaps 112 are shorter in length than the absorbent core 103, they may be selectively positioned anywhere along the side edges 132 of adult incontinence article 101 in a crotch region 110. In one embodiment, the containment flaps 112 extend along the entire length of the absorbent core 103 to better contain the body exudates. Such containment flaps 112 are generally well known to those skilled in the art. For example, suitable constructions and arrangements for the containment flaps 112 are described in U.S. Pat. No. 4,704,116 to Enloe, which is incorporated herein in its entirety by reference thereto for all purposes.

To provide improved fit and to help reduce leakage of body exudates, the adult incontinence article 101 may be elasticized with suitable elastic members, as further explained below. For example, as representatively illustrated in FIG. 3, the adult incontinence article 101 may include leg elastics 106 constructed to operably tension the side margins of the adult incontinence article 101 to provide elasticized leg bands which can closely fit around the legs of the wearer to reduce leakage and provide improved comfort and appearance. Waist elastics 108 may also be employed to elasticize the end margins of the adult incontinence article 101 to provide elasticized waistbands. The waist elastics 108 are configured to provide a resilient, comfortably close fit around the waist of the wearer.

The adult incontinence article 101 may also include one or more fasteners 130. For example, two flexible fasteners 130 are illustrated in FIG. 3 on opposite side edges of waist regions to create a waist opening and a pair of leg openings about the wearer. The shape of the fasteners 130 may generally vary, but may include, for instance, generally rectangular shapes, square shapes, circular shapes, triangular shapes, oval shapes, linear shapes, and so forth. The fasteners may include, for instance, a hook-and-loop material, buttons, pins, snaps, adhesive tape fasteners, cohesives, fabric-and-loop fasteners, etc. In one particular embodiment, each fastener 130 includes a separate piece of hook material affixed to the inside surface of a flexible backing.

The various regions and/or components of the adult incontinence article 101 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the outer cover 117 and bodyside liner 105 are assembled to each other and to the absorbent core 103 using an adhesive. Alternatively, the absorbent core 103 may be connected to the outer cover 117 using conventional fasteners, such as buttons, hook and loop type fasteners, adhesive tape fasteners, and so forth. Similarly, other adult incontinence article components, such as the leg elastic members 106, waist elastic members 108 and fasteners 130, may also be assembled into the adult incontinence article 101 using any attachment mechanism.

Generally speaking, a substrate according to the present invention may be incorporated into the absorbent article in a variety of different orientations and configurations, so long as the device is capable of receiving urine from the wearer and providing a spectral response that a user or caregiver may review for the presence or absence of formaldehyde. For example, the colorants on the substrate may be positioned in the absorbent article so that the colorants are readily visible to the user or caregiver so as to provide a simple, accurate, and real time indication of the presence of the formaldehyde in a urine sample. The visibility of such colorants on the substrate may be accomplished in a variety of ways. For example, in some embodiments, the absorbent article may include a transparent or transluscent portion (e.g., window, film, etc.) that allows the colorants to be readily viewed without removal of the absorbent article from the wearer and/or without disassembly of the absorbent article. In other embodiments, all or part of the colorants may extend through a hole or aperture in the absorbent article for observation. In still other embodiments, the colorants may simply be positioned on a surface of the absorbent article for observation while providing a mechanism for having the colorant in fluid communication with the urine sample.

By way of example, referring again to FIG. 3, in accordance with an exemplary embodiment of the present invention, the adult incontinence article 101 includes a substrate comprising a lateral flow assay device 120 that may be positioned at least partially between the outer cover 117 and the absorbent core 103. The lateral flow assay device 120 may be positioned such that the colorants 136 and 138 are visible through a window 140 in the outercover 117. The sample zone 142, positioned at one end of the assay device 120, is strategically positioned in the adult incontinence article 101 so that urine discharged by the wearer can travel to the sample zone 142 for collection of at least a portion of the discharged urine therein. The absorbent material 154 is also provided at the other end of the assay device 120 to hold part of the sample and to promote wicking or capillary flow in the device 120 as will be more fully described below.

FIG. 3 illustrates the assay device 120 as being placed directly into the layers that comprise the absorbent article 101. Alternatively, the assay device 120 may be partially or completely encased within a thin film (not shown) except for the sample zone 142, which remains exposed to the bodily fluid (e.g., urine) being tested. Such embodiments may be desirable so as to inhibit other components of the assay device 120, other than the sample zone 142, from receiving the bodily fluid directly from the wearer or from the layers of the absorbent article 101. For example, the assay device 120 may operate more effectively if the wicking zone 154 is shielded so that it draws the bodily fluid only from sample zone 142 and not from the absorbent article 101. Such thin film may be constructed, for example, from a variety of materials including polymers such as polyethylene, polypropylene, polycarbonate, and others.

As stated, the assay device 120 is positioned so as to receive the discharged bodily fluid. As shown, the assay device 120 includes a sample zone 142 for collection of the fluid. Alternatively, the sample zone for assay device 120 may be constructed from one or more components that form parts of the absorbent article 101. By way of example, the sample zone could be constructed as part of the surge layer 107, absorbent core 103, or other components that might be used in the construction of absorbent article 101 and that are capable of receiving and providing fluid to assay device 120.

The assay device 120 may be configured with the adult incontinence article 101 in a variety of different placements and orientations. FIG. 3 depicts the assay device 120 at a position between the absorbent core 103 and the outer cover 117. In this manner, the colorants 136 and 138 are visible though the window 140 when the adult incontinence article 101 is in place on the wearer. The window 140 is made of a transparent material formed as part of the outer cover 117 so as to prevent undesirable leaks of the collected fluids. In such cases, the results of testing with the device 120 may be readily observed without removal of the adult incontinence article 101 from the wearer. Alternatively, the device 120 could be placed between, for example, the absorbent core 103 and the bodyside liner 105 with the window 140 being defined by the bodyside liner 105. In such cases, the results of testing with the assay device 120 may be checked when, for example, the adult incontinence article 101 is being changed or replaced on the wearer. Furthermore, the device 120 may be placed at other locations and in different orientations as well.

Figure 4:
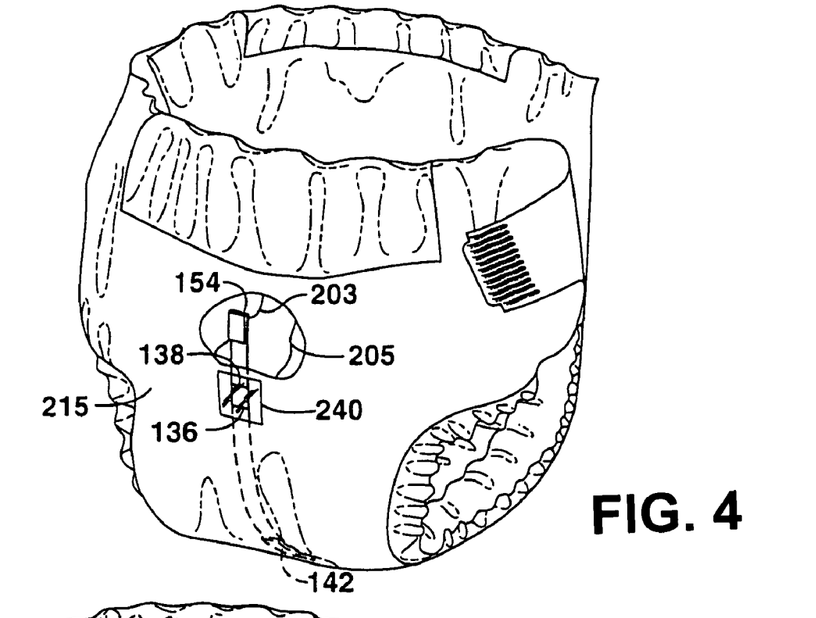

In fact, as will be understood using the present disclosure, numerous exemplary embodiments exist for integrating the assay device 120 into an absorbent article as will be further described. For example, FIG. 4 depicts another exemplary embodiment of the present invention in which the assay device 120 has been integrated into an adult incontinence article 215. Here, a window 240 allows observations of colorants 136 and 138 as previously described. Compared to FIG. 3, the assay device 120 has been placed on an opposite side of the adult incontinence article 101.

Figure 5:
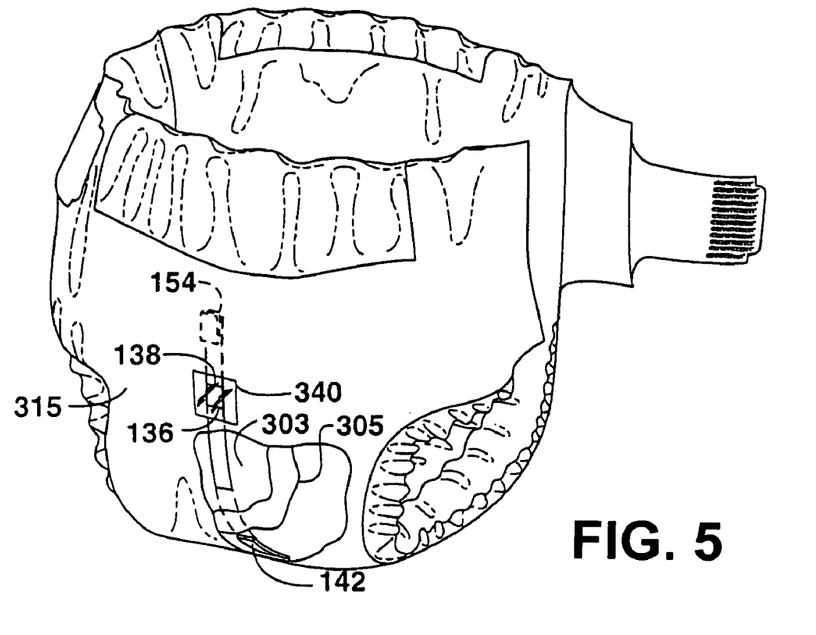

FIG. 5 illustrates another exemplary embodiment where the assay device 120 has been integrated into an adult incontinence article 315. Again, a window 340 allows observations of the colorants 136 and 138 as previously described. In a manner similar to FIG. 3 and FIG. 4, the wicking zone 154 is placed next to the outer cover 117. However, in contrast to FIG. 3 and FIG. 4, the sample zone 142 is placed next to the wearer's skin. More specifically, the adult incontinence article 315 is constructed with the assay device 120 extending through absorbent core 303 and body side liner 305 to a position where sample zone 142 will be adjacent the wearer's skin.

Figure 6:
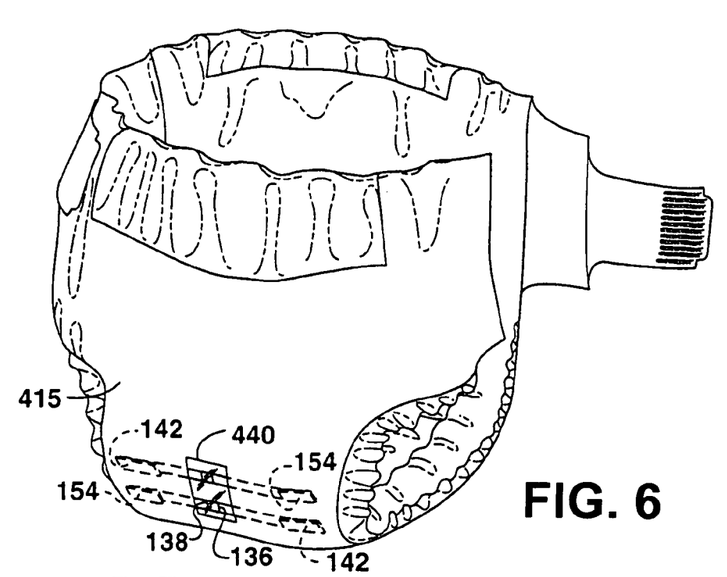

FIG. 6 illustrates an adult incontinence article 415 having two assay devices 120 integrated therein. As shown, window 440 allows the colorants 136 and 138 of two different assay devices 120 to be observed from outside the adult incontinence article 415. Such configuration might be desirable, for example, were each assay device 120 is constructed for detecting the presence of formaldehyde using colorants having different compositions. In addition, the assays devices in FIG. 6 are oriented at an obtuse angle relative to the embodiments of FIGS. 3 through 5. Thus, FIG. 6 also illustrates that multiple configurations and orientations for devices 120 may be utilized under the teachings disclosed herein.

Figure 7:
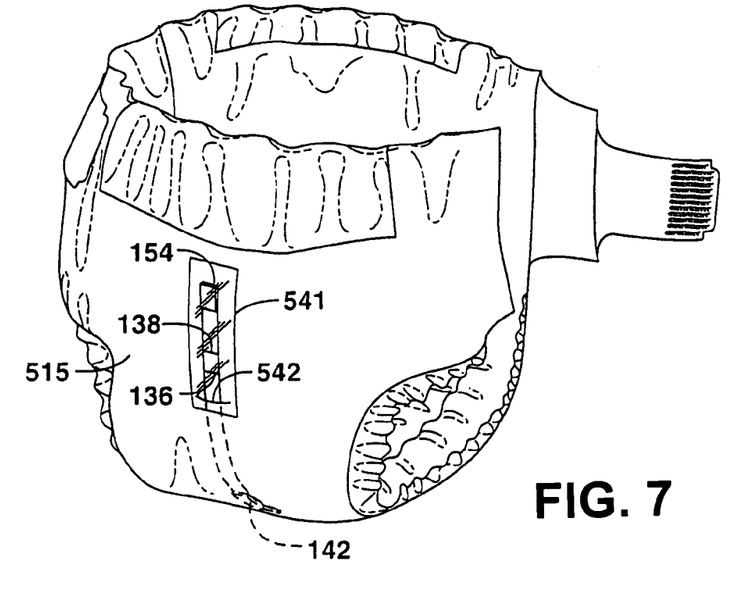

FIG. 7 shows the assay device 120 incorporated into an adult incontinence article 515. Rather than being visible through a window, colorants 136 and 138 are actually on the outside of the adult incontinence article 515. The sample zone 142 resides inside the adult incontinence article 515 as part of the assay device 120 and extends through an aperture 542 in a cover 517. A transparent film 541 is affixed to the cover 517 to protect the assay device 120 and prevent fluid leaks from adult incontinence article 515.

For each of the embodiments described above, the assay device 120 may be fixed into position in the absorbent article using a variety of techniques or mechanisms. For example, the assay device 120 may be attached using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. Alternatively, the assay device 120 may be connected using conventional fasteners, such as buttons, hook and loop type fasteners, adhesive tape fasteners, and so forth.

By way of further example, pockets or apertures may be built into one or more layers of the absorbent article to fix the position of the assay device 120. In short, a variety of configurations may be used to secure assay device 120 into a position that helps ensure contact with the bodily fluid to be tested.

Again, the embodiments of FIGS. 3 through 7 are provided by way of example only as the present invention is not limited to an adult incontinence article and may be used with other absorbents articles as well. In addition, numerous configurations and variations of an assay device may be used. Such assay devices may be incorporated in a variety of orientations and configurations into such absorbent articles.

Regardless of the particular manner in which it is integrated, a fluid such as urine may be directly discharged to a portion of chromatographic medium 123, a liquid permeable cover or other material surrounding assay device 120, or may be discharged onto a component of the absorbent article into which the assay device 120 has been integrated. Once the fluid reaches chromatographic medium 123, the fluid may then travel in the direction illustrated by arrow "L" in FIG. 2. Alternatively, the urine sample may first be applied to, or supplied to, a sample application zone 142 that is in fluid communication with the chromatographic medium 123. The sample application zone 142 may be formed on the medium 123. Alternatively, as shown in FIG. 3, the sample application zone 142 may be formed by a separate material, such as a pad.

After a sufficient reaction time, the intensity of indication (such as a color change) from colorant 136 may be measured to quantitatively or semi-quantitatively determine the level of formaldehyde present in the urine sample. Nevertheless, while quantitative testing may be performed, qualitative testing may be typically employed to provide early testing and monitoring of a health condition. Thus, when formaldehyde is visually detected, the user or caregiver is given an indication that further quantitative testing may be undertaken. For example, an adult incontinence article having an integrated assay device may be periodically used with elderly or non-ambulatory patients as part of a monitoring program that tests for cancer. Upon indication of a positive test result, further quantitative testing can then be undertaken to determine the scope and stage of the problem detected so a to provide additional treatment information.

Figure 8:
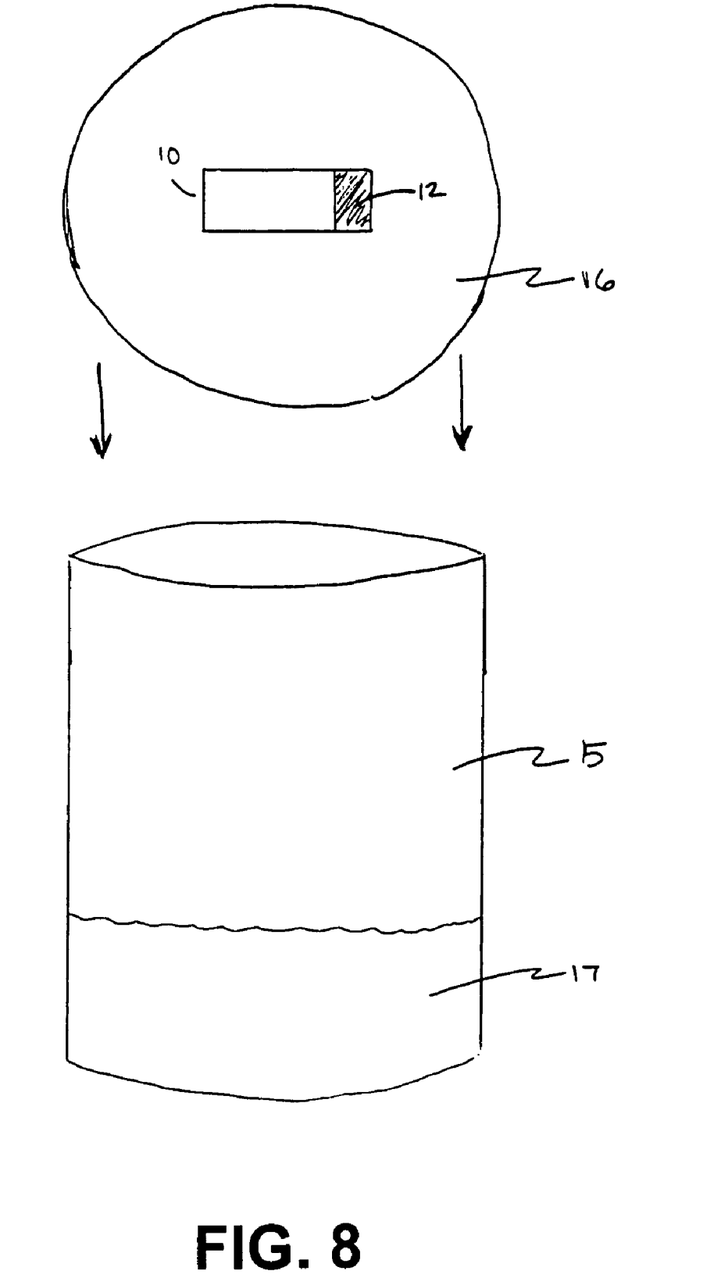
FIG. 8 is a schematic view of another exemplary embodiment of the present invention incorporating a substrate in a sample container.

FIG. 8 illustrates an exemplary embodiment of the present invention in which a substrate 10 has been incorporated into a specimen container 15. Substrate 10 is attached to the inside of lid 16. Upon placing a urine sample 17 into container 15, lid 16 is placed onto container 15 to substantially seal off the interior of container 15. The container 15 is then allowed to equilibrate over a period of time so that substrate 10 can test the vapor from the collected urine sample 17. Upon detecting formaldehyde, colorant 12 provides a spectral response. Lid 16 may be removed to observe colorant 12. Alternatively, an aperture (not shown) having a transparent or translucent covering may be provided so that the colorant 12 of substrate 10 can be observed without removing lid 16 from container 15.

The present invention may be better understood with reference to the following examples.

EXAMPLES

Materials Employed

All reagents and solvents were obtained from Sigma-Aldrich Chemical Company, Inc. of St. Louis, Mo. unless otherwise noted and were used without further purification.

Example 1

The ability of basic fuchsin-sulfuric reagent to indicate the presence of formaldehyde was determined.

The following concentrations of formaldehyde solutions were prepared in water (mg/ml): 5.625, 11.25, 22.5, 45, 90, 180, and 360 mg/ml (which corresponds to 0.056, 1.125, 2.25, 4.5, 9.0, 18.0 and 36.0 percent, respectively). For each concentration of formaldehyde solution, 50 μl was placed into a microtiter well. In addition, water without any formaldehyde was also placed into one of the microtiter wells as a control.

Separately, basic fuchsin-sulfuric acid reagent was prepared by mixing 150 µl of 2.0 mg/ml stock solution of basic fuchsin in ethanol with 2.0 ml of water. This produced a solution red in color. This mixture was then slowly combined with 2N sulfuric acid until the red colored solution became colorless.

Figure 9:
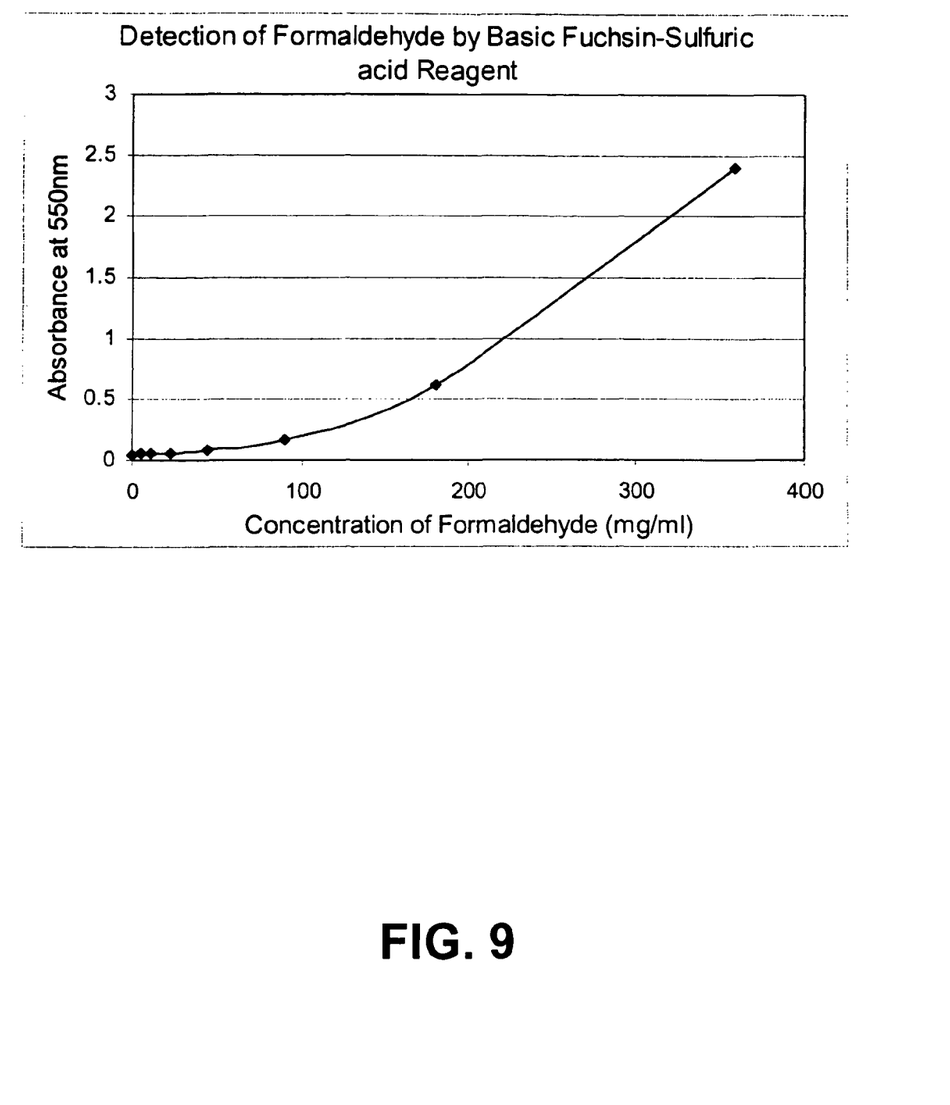
FIG. 9 is the dose response curve that shows the absorbance reading versus concentration for Example 1.

Next, 250 µl of the basic fuchsin-sulfuric acid reagent was added into each of the microtiter wells containing formaldehyde and mixed for less than about two minutes. Each well was then read at 550 nm using a microplate reader and the results are provided in FIG. 9. It was also visually observed that the formaldehyde solutions generated a pink color in a dose response manner after mixing with the reagent.

Example 2

The ability to use basic fuchsin-sulfuric reagent without indicating the presence of other aldehydes was determined.

The following concentrations of aldehydes were prepared in water: 1.0 mg/ml of acetaldehyde, 15.0 mg/ml of isovaleraldehyde, 15.0 mg/ml of phenlyacetaldehyde, and 5.0 mg/ml of phthalic dicarboxyaldehyde. For each concentration, 50 µl was placed into a microtiter well. Basic fuchsin-sulfuric acid reagent was prepared as previously described, and 250 µl was added into each of the microtiter wells. No significant color change was observed in any of the wells.

Example 3

The ability to immobilize or coat basic fuchsin-sulfuric reagent onto a substrate was determined.

A sheet of KIMWIPE® was coated with basic fuchsin-sulfuric agent prepared in a manner was previously described. The sheet was allowed to air dry. Various concentrations of formaldehyde were prepared and applied to different portions of the sheet. Where the formaldehyde solution was applied, a visible pink color change was generated in a dose dependent manner.

Example 4

The ability to use basic fuchsin immobilized onto a substrate to test for the presence of formaldehyde in the headspace of a liquid was determined.

Basic fuchsin was mixed with water to create a solution of approximately 0.001-0.002 weight percent of the dye. Whatman filter paper was then cut into strips and dipped into each solution. The strips were hung in a fume hood for several hours until dry.

Separately, water and a 38% neat solution of formaldehyde were used to create the following urine samples of formaldehyde: 38%, 3.8%, 0.38%, 0.038%, 0.0038%, 0.00038 percent, and 0.000038 percent.

Using a pipette, 1 ml of each formaldehyde solution was placed into a glass vial. Dye coated strips were then placed into the headspace of each vial by hanging the strip over the edge of the vial while screwing the caps into place such that the strip was suspended in the headspace without touching the liquid. Each vial was then left at room temperature overnight. Subsequently, a visible color change on each strip was compared to a water control. Visible changes in the strip color were perceived for each formaldehyde concentration down to the 0.000038% concentration.

A handheld spectrophotometer was then used to calculate a $\Delta E$ value based on $\Delta L^*$, $\Delta a^*$, and $\Delta b^*$ for each strip placed over a formaldehyde solution and the strip placed over the water control. The $\Delta E$ values confirmed the perceived visual changes as values of approximately 5 or higher correspond to changes that are perceptible to the naked eye. As clinically significant values of formaldehyde have been reported at ppm and ppb values, the ability of basic fuchsin as an indicator of formaldehyde was demonstrated.

Example 5

The ability to use chrysoidin immobilized onto a substrate to test for the presence of formaldehyde in the headspace of a liquid was determined. Sample test strips were prepared and tested as previously described with regard to example 3, except the test strips were prepared using a solution of 0.001-0.002 weight percent chrysoidin in water. Visible changes in the strip color were perceived for each formaldehyde concentration down to the 0.000038% concentration with $\Delta E$ values confirming the perceived visual changes. Thus, as clinically significant values of formaldehyde have been reported at ppm and ppb values, the ability of chrysoidin as an indicator for formaldehyde was demonstrated.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method for detecting formaldehyde in a urine sample, the method comprising:
catching a flow of urine from an individual in an absorbent article, the absorbent article comprising a device that contains a substrate, the substrate defining a sample application zone for receiving the urine and a discrete detection zone located downstream from the sample application zone and within which is located a colorant, wherein the urine contacts the sample application zone of the substrate and flows therethrough to reach the colorant within the detection zone, and wherein the colorant reacts directly with formaldehyde to produce a visible spectral response; and
visually detecting the spectral response.

2. The method of claim 1, wherein the colorant includes a triarylmethane.

3. The method of claim 2, wherein the triarylmethane includes pararosanilin or an analog thereof.

4. The method of claim 2, wherein the colorant includes basic fuchsin.

5. The method of claim 2, wherein the triarylmethane is pre-reacted with a sulfur-containing compound.

6. The method of claim 1, wherein the colorant comprises an aromatic azo compound.

7. The method of claim 6, wherein the aromatic azo compound comprises chrysoidin.

8. The method of claim 1, wherein the substrate is a chromatographic medium of a lateral flow device.

9. The method of claim 1, wherein the spectral response is detected and compared to a control colorant.

10. The method of claim 1, wherein the spectral response is correlated to the presence of formaldehyde at a concentration of about 10 parts per billion or more.

11. The method of claim 1, wherein the spectral response is produced in about 5 minutes or less after the substrate is contacted with the urine.

12. The method of claim 1, wherein the sample application zone is located adjacent to or is part of an absorbent core of the absorbent article.

13. The method of claim 1, wherein the substrate is positioned between a substantially liquid impermeable layer and an absorbent core of the absorbent article.

14. The method of claim 1, wherein the substrate is positioned between a liquid permeable layer and an absorbent core of the absorbent article.

15. The method of claim 1, wherein the substrate is adhered to the absorbent core.

16. The method of claim 1, wherein the detection zone is in the shape of a stripe, band, dot, or a combination thereof.

17. The method of claim 1, wherein the spectral response is correlated to the presence of formaldehyde.

18. The method of claim 1, wherein the substrate is in the form of a strip and the detection zone is in the form of a band that extends along a width of the strip.

19. The method of claim 1, wherein the sample application zone is in fluid communication with an absorbent core of the absorbent article.

20. The method of claim 1, wherein the absorbent article is a personal care absorbent article.

21. The method of claim 20, wherein the personal care absorbent article is a diaper, training pants, absorbent underpants, incontinence article, feminine hygiene product, swim wear, or a baby wipe.

22. The method of claim 20, wherein the absorbent article is a medical article, food service wiper, or a clothing article.

* * * * *